United States Patent [19]

Aly

[11] Patent Number: 4,548,640
[45] Date of Patent: Oct. 22, 1985

[54] ALLYLTHIODIPHENYL ETHER HERBICIDES

[75] Inventor: Elsayed A. Aly, Holland, Pa.

[73] Assignee: FMC Corporation, Philadelphia, Pa.

[21] Appl. No.: 544,321

[22] Filed: Oct. 21, 1983

[51] Int. Cl.⁴ .................... A01N 31/08; C07C 149/34
[52] U.S. Cl. ......................................... 71/98; 71/103; 568/30; 568/31; 568/33; 568/36; 568/37; 568/39; 568/43; 568/44; 568/52
[58] Field of Search .................. 568/27, 34, 44; 71/98

[56] References Cited

U.S. PATENT DOCUMENTS

| 4,277,624 | 7/1981 | Yoshimoto et al. | 568/44 |
|---|---|---|---|
| 4,401,461 | 8/1983 | Wilson et al. | 71/98 |
| 4,419,122 | 12/1983 | Swithenbank | 71/98 |

FOREIGN PATENT DOCUMENTS

| 3212165 | 6/1983 | Fed. Rep. of Germany . | |
| 48-26208 | 8/1973 | Japan | 71/98 |
| 79723 | 7/1976 | Japan . | |
| 51-79723 | 7/1976 | Japan . | |
| 52-28934 | 3/1977 | Japan | 71/98 |
| 2926829 | 1/1980 | Netherlands | 71/98 |

OTHER PUBLICATIONS

Aoki, Yukio, et al., Chem Abst., vol. 86 (1977), 12706y, equiv. Japan 7679723.
Derwent Abstract No. 65550X/35; Japan Kokai 51079723.
Chem. Abstract, Abstract No. 90: 198873m; Japan Kokai 7905033.
Derwent Abstract No. 05700C/04; German OLS 2926829.

Primary Examiner—Robert Gerstl
Assistant Examiner—Cecilia Shen
Attorney, Agent, or Firm—William Schmonsees; H. Robinson Ertelt; Robert L. Andersen

[57] ABSTRACT

Novel allylthiodiphenyl ether compounds exhibit excellent herbicidal activity against broadleaf weeds while leaving crops such as corn, wheat, rice and soybeans unaffected. Preparation and herbicidal activity of the compounds is disclosed and exemplified.

4 Claims, No Drawings

ALLYLTHIODIPHENYL ETHER HERBICIDES

The present invention relates to novel allylthiodiphenyl ether herbicides, to herbicidal compositions thereof, and to a method for controlling growth of undesired plants generally found in connection with growing agricultural and/or horticultural crops.

Diphenyl ethers have been known for many years to be useful preemergent or postemergent herbicides for controlling weeds in agricultural crops, and several such compounds are available for use on a limited number of crops.

The present invention provides a group of diphenyl ethers in which one of the phenyl rings is substituted with a chloro or nitro group and an adjacent optionally substituted allylthio group. The novel compounds of the present invention may thus be represented by the formula

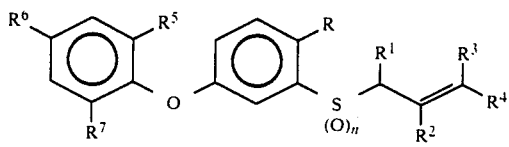

in which:

R is chloro or nitro $R^1$, $R^2$, $R^3$, and $R^4$ are independently selected from hydrogen; halogen; lower alkyl; lower haloalkyl; lower alkoxy; cyano; lower alkylcarbonyl; a carboxyl group of the formula —COOM in which M is hydrogen, a lower alkyl or haloalkyl group, or an agriculturally acceptable salt-forming cation such as an alkali metal, an alkaline earth metal, an ammonium ion, a sulfonium ion or sulfoxonium ion, a phosphonium ion or a protonated amine such as triethylamine or triisopropylamine; a group of the formula —S(O)$_n$R$^8$ in which R$^8$ is lower alkyl or lower haloalkyl; or R$^1$ and R$^2$ are hydrogen and R$^3$ and R$^4$ taken together form a=CH$_2$ group or taken together with the included carbon form a cycloalkyl group of 5–8 carbon atoms.

$R^5$ is a halogen atom such as chloro, $R^6$ is halogen or trifluoromethyl, $R^7$ is hydrogen or halogen, and n is an integer having a value of 0, 1, or 2.

As used throughout this specification the following terms have the meanings indicated below unless a contrary intent is clearly expressed. The terms "halo" or "halogen", alone or as part of a larger group, means an atom selected from chlorine, bromine and fluroine. The term "lower" as applied to a hydrocarbyl group, alone or as part of a larger group, means a group having 1 to 4 carbon atoms.

The following examples illustrate preparation of the compounds of the invention.

EXAMPLE 1

Synthesis of 3-allylthio-4-nitrophenyl 2-chloro-4-trifluoromethylphenyl ether (Compound 1)

Part A Synthesis of 2-chloro-4-trifluoromethylphenol

In 150 ml of dimethyl sulfoxide 21.5 g (0.1 mole) of α,α,α-trifluoror-3,4-dichlorotoluene, 11.2 g (0.2 mole) of powdered potassium hydroxide, and 10 ml of tertiary butyl alcohol were heated at 75° C. for approximately seventeen hours. The reaction mixture was cooled, poured over ice, and extracted with toluene. The aqueous phase was separated, mixed with 50 ml of chloroform, and acidified with concentrated hydrochloric acid. The chloroform layer was separated and dried over anhydrous sodium sulfate. The chloroform was removed under reduced pressure, leaving a liquid residue. Distillation at 55° C./1.2 mm of Hg yielded 10.8 g of 2-chloro-4-trifluoromethylphenol. The nmr spectrum was consistent with the proposed structure.

Part B Synthesis of 2-allylthio-4-fluoronitrobenzene

A solution of 2.3 g (0.031 mole) of allylthiol in 25 ml of tetrahydrofuran was added to 5.0 g (0.031 mole) of 2,4-difluoronitrobenzene in 25 ml of tetrahydrofuran at −30° C. To this mixture was added dropwise 3.1 g (0.031 mole) of triethylamine. The temperature was allowed to rise to room temperature and stirring was continued for four hours. The tetrahydrofuran was evaporated under reduced pressure, and water and diethyl ether were added to the residue. The ether layer was separated and dried over anhydrous potassium carbonate. The ether was evaporated under reduced pressure, leaving a liquid residue. This residue was distilled at 105° C./1.2 mm of Hg, yielding 4.2 g of 2-allylthio-4-fluoronitrobenzene. The nmr spectrum was consistent with the proposed structure.

Part C Synthesis of 3-allylthio-4-nitrophenyl 2-chloro-4-trifluoromethylphenyl ether.

Under nitrogen 1.85 g (0.00939 mole) of 2-chloro-4-trifluoromethylphenol (Part A) and 1.2 g (0.0087 mole) of potassium carbonate were stirred overnight in 25 ml of dimethyl sulfoxide. To this mixture was added 2.0 g (0.0094 mole) of 2-allylthio-4-fluoronitrobenzene (Part B) and the reaction mixture was stirred at room temperature for seventy-two hours. The reaction mixture was poured into cold water which was then extracted with diethyl ether. The ether layer was separated, washed twice with water, and dried over anhydrous sodium sulfate. The ether was evaporated under reduced pressure, leaving a liquid residue. This residue was distilled using a short path distillation head to yield 2.2 g of 3-allylthio-4-nitophenyl 2-chloro-4-trifluoromethyl ether.

NMR spectrum (CDCl$_3$; ppm): 3.6(d,2H); 5.2–5.8(m,3H); 6.9–8.4(m,6H)

Elemental Analysis for C$_{16}$H$_{11}$NClF$_3$O$_3$S: Calc'd: C 49.30; H 2.84; N 3.59; Found: C 49.33; H 2.67; N 3.27.

EXAMPLE 2

Synthesis of 3-(2-methyl-2-propenylthio)-4-nitrophenyl 2-chloro-4-trifluoromethylphenyl ether (Compound 2)

Part A Synthesis of 2-(2-methyl-2-propenylthio)-4-fluoronitrobenzene

To a solution of 5.0 g (0.031 mole) of 2,4-difluoronitrobenzene and 2.8 g (0.031 mole) of 2-methyl-2-propenethiol in 25 ml of tetrahydrofuran at room temperature was added dropwise 3.1 g (0.031 mole) of triethylamine. The reaction mixture was stirred at room temperature for forty-eight hours and then at 50° C. for eight hours. The tetrahydrofuran was removed under reduced pressure, and water was mixed with the residue. This aqueous mixture was extracted with chloroform. The chloroform extract was washed with water, dried, and the chloroform evaporated under reduced pressure, leaving an oily residue. Distillation of this residue under reduced pressure yielded 6.0 g of 2-(2-methyl-2-propenylthio)-4-fluoronitrobenzene. The nmr spectrum was consistent with the proposed structure.

Part B Synthesis of 3-(2-methyl-2-propenylthio)-4-nitrophenyl 2-chloro-4-trifluoromethylphenyl ether A mixture of 1.85 g (0.00939 mole) of 2-chloro-4-trifluoromethylphenol (Example 1, Part A), 2.1 g (0.0093 mole) of 2-(2-methyl-2-propenylthio)-4-fluoronitrobenzene (Part A), and 1.3 g (0.0094 mole) of potassium carbonate in 25 ml of dimethyl formamide was stirred at 60° C. for three hours. The mixture was poured into water and extracted with chloroform. The chloroform extract was washed with water and dried over anhydrous magnesium sulfate. After filtration, the chloroform was evaporated under reduced pressure. The residue was subjected to a hagh vacuum, leaving 2.5 g of 3-(2-methyl-2-propenylthio)-4-nitrophenyl 2-chloro-4-trifluoromethylphenyl ether as an oil.

NMR spectrum (CDCl$_3$; ppm): 1.9(d,3H); 3.6(s,2H); 5.2(d,2H); 6.9–8.4(m,6H).

Elemental Analysis for C$_{17}$H$_{13}$NClF$_3$O$_3$S: Calc'd: C 50.57; H 3.24; N 3.47; Found: C 50.21; H 3.09; N 3.23.

EXAMPLE 3

Synthesis of 3-(2-methyl-2-propenylsulfinyl)-4-nitrophenyl 2-chloro-4-trifluoromethyl ether (Compound 3)

To a solution of 2.0 g (0.0048 mole) of 3-(2-methyl-2-propenylthio)-4-nitrophenyl 2-chloro-4-trifluoromethylphenyl ether (Example 2, Step B) in 25 ml of methylene chloride at 0° C. was added dropwise a solution of 1.0 g (0.0048 mole) of m-chloroperbenzoic acid (85% purity) in 10 ml of methylene chloride. The reaction mixture was stirred at room temperature for three hours. The mixture was shaken with a 10% aqueous solution of sodium bicarbonate until it was slightly basic. The organic layer was separated, washed with water, and dried. Evaporation of the methylene chloride under reduced pressure left 1.8 g of 3-(2-methyl-2-propenylsulfinyl)-4-nitrophenyl 2-chloro-4-trifluoromethylphenyl ether as an oily residue.

NMR spectrum (CDCl$_3$; ppm): 1.9(d,3H); 4.2(s,2H); 5.2(d,2H); 6.9–8.4(m,6H).

Elemental Analysis for C$_{17}$H$_{13}$NClF$_3$O$_4$S: Calc'd: C 48.64; H 3.12; N 3.33; Found: C 48.49; H 2.96; N 3.01.

BIOLOGICAL EVALUATION

The test species used in demonstrating the herbicidal activity of the compounds of this invention were lima bean (*Phaseolus limensis*), soybean (*Glycine max*), cotton (*Glossypium hirsutum*), field corn (*Zea mays*), wheat (*Triticum aestivum*), rice (*Oryza sativa*), field bindweed (*Convolvulus arvensis*), morningglory (*Ipomoea lacunosa*), velvetleaf (*Abutilon theophrastri*), barnyard grass (*Echinochloa crus-galli*), green foxtail (*Setaria viridis*), johnsongrass (*Sorghum halepense*), yellow nutsedge (*Cyperus esculentus*), bermuda grass (*Cynodon dactylon*), cocklebur (*Xanthium pensylvanicum*), giant foxtail (*Setaria faberii*), hairy crabgrass (*Digitaria sanguinalis*), jimsonweed (*Datura stramonium*), lambsquarter (*Chenopodium album*), nightshade (*Solanum sp.*), purslane (*Portulaga oleracea*), pigweed (*Amaranthus retroflexus*), hemp sesbania (*Sesbania exaltata*), wild mustard (*Brassica kaber*), broadleaf signalgrass (*Brachiaria platyphylla*), and yellow foxtail (*Setaria lutescens*).

For the preemergence tests, seeds of the test species were planted in 15×20×8-cm flats containing approximately a 5-cm depth of sandy loam soil. Prior to seeding, the rows were marked by pressing a wooden template onto the soil surface. After sowing, a fungicidal treatment was sprinkled onto the seeds, and a thin layer of soil (approximately 1.0 cm) was applied to the surface of the flat. The spray solutions containing the compounds of the invention were then applied directly to the soil as aqueous acetone solutions at rates equivalent to 8.00 kilograms active ingredient per hectare and submultiples thereof (4.00 kg/ha, 2.00 kg/ha, 1.00 kg/ha, 0.50 kg/ha).

The test plants were maintained in a greenhouse and watered regularly on the soil surface for two to three weeks, at which time phytotoxicity was observed and recorded. Results are shown in Table I.

For postemergence tests, seeds of plant species were seeded in the flats as for preemergence tests, covered with a thin layer (approximately 1.0 cm) of soil, and placed in the greenhouse. They were watered regularly for 10 to 14 days, at which time the spray solutions containing the compounds of the invention were applied to the plants as aqueous acetone solutions. The treated plants were maintained in the greenhouse and watered regularly for an additional 10 to 14 days, after which the phytotoxicity was observed and recorded. Results are shown in Table 2.

In the preemergent tests the soybean, cotton, field corn and rice all tolerated compound 1 extremely well whereas wheat and lima bean were substantially less tolerant. Some of the weed species were well controlled. These results indicate that compound 1 of the invention is useful for use as a preemergent herbicide to control weeds such as lambsquarter and pigweed and nightshade.

The postemergent tests reported in table 2 illustrate that crops such as soybean, corn, rice, and wheat tolerate the compounds of the invention extremely well. Broadleaf weeds were readily controlled in general, whereas grasseous weeds are less susceptible to adequate control at low use rates.

The foregoing illustrates that compounds of this invention are particularly useful as postemergent herbicides, particularly for grasseous crops such as corn, wheat and rice, but also for broadleaf crops such as soybeans. In these crops the compounds exhibit unusually broad spectrum of control of undesired vegetation, particularly of broadleaf weeds such as bindweed, velvetleaf, cocklebur, morningglory, nightshade, and the like at very low application rates.

For herbicidal application the compounds of this invention will not ordinarily be applied in undiluted form, but will be diluted or extended with an agriculturally acceptable, relatively inert material, here called a carrier, which may be liquid or solid. Thus the compounds of this invention may be utilized in diverse formulations prepared from agricultural adjuvants and agricultural carriers to give the herbicidal compositions contemplated herein. The herbidcidal compositions contain between about 0.01% and 95% active ingredient together with between about 4% and 98.5% agriculturally acceptable carrier and between about 1% and 15% surface active agent by weight. As is well-known in the art, the formulation and mode of application of a toxicant may affect the activity of the material in a given application. Thus, a compound of this invention may be formulated as an emulsifiable concentrate, as a granule of relatively large particle size, as a wettable powder, as a solution, or as any of several other known types of formulations, depending on the desired mode of application.

Emulsifiable concentrates are homogeneous liquid or paste compositions dispersible in water or other dispersant, and may consist entirely of a compound of this invention with a liquid or solid emulsifying agent, or may also contain an agriculturally acceptable liquid carrier, such as xylene, heavy aromatic naphthas, isophorone and other non-volatile organic solvents.

Granular formulations are particularly useful for aerial distribution. Useful granular formulations may be of several types. Impregnated granules are those wherein the active ingredient is applied to large particles of an absorbent carrier, such as an attapulgite or kaolin clay, corncobs, expanded mica, normally in the form of a solution in a solvent. Surface-coated granules may be produced by spraying the molten active ingredient onto the surface of a generally nonabsorbent particle or by spraying on a solution of active ingredient in a solvent. The core may be water-soluble such as a prilled fertilizer, or insoluble such as sand, marble chips or coarse talc. Particularly useful is a granule wherein a wettable powder is applied as a surface coating to a sand or other insoluble particle such that the wettable powder may be dispersed on contact of the granule with moisture. Granules may be produced by agglomeration of dusts or powders by compaction rollers, by extrusion through a die or by use of a granulating disc. Granular formulations may vary widely in concentration, with useful formulations containing as little as 0.5% or as much as 95% of active ingredient.

Wettable powders, also useful formulations for herbicides, are in the form of finely divided particles which disperse readily in water or other dispersants. The wettable powder is ultimately applied to the soil as a finely divided dry material or as an emulsion in water or other liquid. Typical carriers for wettable powders include fuller's earth, kaolin clays, silicas and other highly absorbent, readily wet inorganic diluents. Wettable powders normally are prepared to contain about 5% to 80% of active ingredient, depending on the absorbability of the active ingredient and on the absorbency of the carrier, and usually also contain a small amount of a wetting, dispersing or emulsifying agent to facilitate dispersion.

Typical wetting, dispersing or emulsifying agents used in agricultural formulations include, for example, the alkyl and alkylaryl sulfonates and sulfates and their sodium salts; polyethylene oxides; sulfonated oils, fatty acid esters of polyhydric alcohols; and other types of surface active agents, many of which are available in commerce.

The surface-active agent, when used, normally comprises from 1% to 15% by weight of the herbicidal composition.

These formulations may be applied without further dilution or as dilute solutions, emulsions or suspensions in water or other suitable diluent. The compositions may be applied to the area wherein control is desired by spraying onto the surface of the soil in the case of liquid compositions or by distribution from mechanical equipment in the case of solids. The surface-applied material may also be blended into the upper layer of soil by cultivation, or left as applied, as is appropriate to gain the optimum results with the particular treatment.

The active herbicidal compounds of this invention may be formulated and/or applied with insecticides, fungicides, nematicides, plant regulators, fertilizers, and other agricultural chemicals. In applying the active compounds of this invention, whether formulated alone or with other agricultural chemicals, an effective amount and concentration of active ingredient are of course employed. The amount constituting an effective amount is variable, depending on a number of factors such as the type of soil, the expected pattern of rainfall or irrigation, the plant species to be controlled, and the crop, if any, to be grown. Generally, a uniform application of between 0.1 and 9 kilograms per hectare will be employed, for example, 0.125 to 2.00 kilograms per hectare.

It is apparent that various modifications may be made in the formulation and application of the novel compounds of this invention, without departing from the inventive concept herein, as defined in the claims.

TABLE 1

Preemergence Herbicidal Activity of Compound 1

| | Application Rate of Compound 1 (kg/ha) | | | | | | | |
|---|---|---|---|---|---|---|---|---|
| | 8 | | 4 | | 2 | | 1 | |
| Species | $V^a$ | $K^b$ | $V^a$ | $K^b$ | $V^a$ | $K^b$ | $V^a$ | $K^b$ |
| Lima Bean | 3 | 90 | | | | | | |
| Soybean | 4 | 0 | 5 | 0 | 5 | 0 | 5 | 0 |
| Cotton | 4 | 0 | 5 | 0 | 5 | 0 | 5 | 0 |
| Field Corn | 5 | 0 | 5 | 0 | 5 | 0 | 5 | 0 |
| Wheat | 3 | 40 | 3 | 60 | 3 | 60 | 3 | 60 |
| Rice | 5 | 0 | 5 | 0 | 5 | 0 | 5 | 0 |
| Files Bindweed | 0 | 100 | 4 | 20 | 4 | $77^c$ | 5 | 0 |
| Morningglory | 3 | $97^c$ | 2 | 80 | 2 | 80 | 5 | 0 |
| Velvetleaf | 0 | 100 | 0 | 100 | 3 | 80 | 5 | 0 |
| Barnyardgrass | 4 | 0 | 5 | 0 | 5 | 0 | 5 | 0 |
| Green Foxtail | 0 | 100 | 4 | 60 | 4 | 40 | 5 | 0 |
| Johnsongrass | 0 | 100 | 3 | 70 | 3 | 30 | 3 | 60 |
| Yellow Nutsedge | 5 | 0 | 5 | 0 | 5 | 0 | 5 | 0 |
| Bermuda Grass | 5 | 0 | | | | | | |
| Cocklebur | | | | | 4 | 50 | 5 | 0 |
| Giant Foxtail | | | | | 0 | 100 | 4 | 30 |
| Hairy Crabgrass | | | | | 4 | 90 | 4 | 50 |
| Jimsonweed | | | | | 4 | 20 | 5 | 0 |
| Lambsquarter | | | | | 0 | 100 | 0 | 100 |
| Nightshade | | | | | 0 | 100 | 4 | 60 |
| Purslane | | | | | 4 | 10 | 5 | 0 |
| Pigweed | | | | | 0 | 100 | 0 | 100 |
| Hemp Sesbania | | | | | 4 | 50 | 4 | 0 |
| Wild Mustard | | | | | 0 | 100 | 5 | 0 |

$^a$ V = Vigor, rated as follows:

| Rating | Meaning |
|---|---|
| 0 | Plants did not survive |
| 1 | Severe injury; plants not expected to recover |
| 2 | Moderate to severe injury; plants not expected to recover |
| 3 | Moderate injury plants are expected to recover with time |
| 4 | Slight injury; plants have recovered or are expected to fully recover |
| 5 | No or minimal adverse effects on plants |

$^b$ K = percent kill.
$^c$ Average value

TABLE $2^a$

Postemergence Herbicidal Activity

| | | Compound | | | | | |
|---|---|---|---|---|---|---|---|
| | Rate | 1 | | 2 | | 3 | |
| Species | (kg/ha) | $V^a$ | $K^b$ | $V^a$ | $K^b$ | $V^a$ | $K^b$ |
| Lima Bean | 8 | 0 | 100 | | | | |
| Soybean | 8 | 3 | $40^c$ | | | | |
| | 4 | 4 | 40 | 4 | 0 | 5 | 0 |
| | 2 | 4 | $12^c$ | 4 | 0 | 5 | 0 |
| | 1 | 4 | $8^c$ | 5 | 0 | 5 | 0 |
| Cotton | 4 | 0 | 100 | 0 | 100 | 0 | 100 |
| | 2 | 4 | 100 | 3 | 80 | 0 | 100 |
| | 1 | 0 | 100 | 3 | 80 | 0 | 100 |
| Field Corn | 8 | 5 | 0 | | | | |
| | 4 | 5 | 0 | 5 | 0 | 5 | 0 |
| | 2 | 4 | 32 | 5 | 0 | 5 | 0 |
| | 1 | 5 | 0 | 5 | 0 | 5 | 0 |
| Rice | 8 | 5 | 0 | | | | |

TABLE 2a-continued

Postemergence Herbicidal Activity

| Species | Rate (kg/ha) | Compound 1 $V^a$ | Compound 1 $K^b$ | Compound 2 $V^a$ | Compound 2 $K^b$ | Compound 3 $V^a$ | Compound 3 $K^b$ |
|---|---|---|---|---|---|---|---|
| | 4 | 5 | 0 | 5 | 0 | 5 | 0 |
| | 2 | 5 | 0 | 5 | 0 | 5 | 0 |
| | 1 | 5 | 0 | 5 | 0 | 5 | 0 |
| Wheat | 8 | 3 | 45$^c$ | | | | |
| | 4 | 4 | 40 | 5 | 0 | 4 | 20 |
| | 2 | 3 | 72$^c$ | 5 | 0 | 4 | 20 |
| | 1 | 4 | 22$^c$ | 5 | 0 | 5 | 0 |
| Field Bindweed | 8 | 0 | 100 | | | | |
| | 4 | 0 | 100 | 4 | 60 | 0 | 100 |
| | 2 | 0 | 100 | 4 | 30 | 0 | 100 |
| | 1 | 4 | 95$^c$ | 5 | 0 | 0 | 100 |
| Morning-glory | 8 | 0 | 100 | | | | |
| | 4 | 0 | 100 | 3 | 90 | 3 | 90 |
| | 2 | 0 | 100 | 3 | 80 | 4 | 90 |
| | 1 | 4 | 90$^c$ | 4 | 80 | 4 | 90 |
| Velvet-leaf | 8 | 0 | 100 | | | | |
| | 4 | 0 | 100 | 0 | 100 | 0 | 100 |
| | 2 | 3 | 94$^c$ | 4 | 80 | 3 | 90 |
| | 1 | 4 | 95$^c$ | 0 | 100 | 0 | 100 |
| Barnyard-grass | 8 | 3 | 85$^c$ | | | | |
| | 4 | 0 | 100 | 4 | 0 | 5 | 0 |
| | 2 | 4 | 30 | 4 | 0 | 5 | 0 |
| | 1 | 5 | 0 | 5 | 0 | 5 | 0 |
| Green Foxtail | 8 | 3 | 97$^c$ | | | | |
| | 4 | 0 | 100 | 4 | 50 | 0 | 100 |
| | 2 | 4 | 82$^c$ | 4 | 10 | 4 | 50 |
| | 1 | 4 | 52$^c$ | 5 | 0 | 4 | 80 |
| Johnson-grass | 8 | 4 | 0 | | | | |
| | 4 | 5 | 0 | 5 | 0 | 4 | 0 |
| | 2 | 3 | 48$^c$ | 5 | 0 | 5 | 0 |
| | 1 | 4 | 14$^c$ | 5 | 0 | 5 | 0 |
| Yellow Nutsedge | 8 | 5 | 0 | | | | |
| | 4 | 5 | 0 | 5 | 0 | 5 | 0 |
| | 2 | 5 | 0 | 5 | 0 | 5 | 0 |
| | 1 | 5 | 0 | 5 | 0 | 5 | 0 |
| Hemp | 4 | 0 | 100 | | | | |

TABLE 2a-continued

Postemergence Herbicidal Activity

| Species | Rate (kg/ha) | Compound 1 $V^a$ | Compound 1 $K^b$ | Compound 2 $V^a$ | Compound 2 $K^b$ | Compound 3 $V^a$ | Compound 3 $K^b$ |
|---|---|---|---|---|---|---|---|
| Sasbania | 2 | 0 | 100 | | | | |
| | 1 | 0 | 100 | | | | |
| Bermuda Grass | 8 | 4 | 0 | | | | |
| Cocklebur | 2 | 3 | 95$^c$ | | | | |
| | 1 | 3 | 53$^c$ | | | | |
| Giant Foxtail | 2 | 4 | 97$^c$ | | | | |
| | 1 | 4 | 92$^c$ | | | | |
| Hairy Crabgrass | 2 | 5 | 0 | | | | |
| | 1 | 5 | 0 | | | | |
| Jimson-weed | 2 | 0 | 100 | | | | |
| | 1 | 0 | 100 | | | | |
| Night-shade | 2 | 0 | 100 | | | | |
| | 1 | 0 | 100 | | | | |
| Purslane | 2 | 0 | 100 | | | | |
| | 1 | 0 | 100 | | | | |
| Sicklepod | 2 | 4 | 10 | | | | |
| | 1 | 4 | 15$^c$ | | | | |
| Wild Mustard | 2 | 0 | 100 | | | | |
| | 1 | 3 | 97$^c$ | | | | |
| Broadleaf Signalgrass | 2 | 4 | 10 | | | | |
| | 1 | 4 | 40$^c$ | | | | |
| Yellow Foxtail | 2 | 4 | 60 | | | | |
| | 1 | 4 | 87$^c$ | | | | |

$^{a,b,c}$ - See footnotes to table 1.

I claim:

1. The compound 3-allylthio-4-nitrophenyl 2-chloro-4-trifluoromethylphenyl ether.

2. A heribicidal composition comprising an herbicidally effective amount of the compound of claim 1 in admixture with at least one compatible agriculturally acceptable carrier.

3. A method for controlling undesired broadleaf plant growth which comprises applying to the locus where control is desired an herbicidally effective amount of the compound of claim 1.

4. The method of claim 3 in which said compound is applied at a rate of 0.1 to 0.5 kg/ha.

* * * * *